United States Patent [19]

Keyes

[11] B 4,001,085

[45] Jan. 4, 1977

[54] IMMOBILIZATION OF ENZYMES ON AN INORGANIC MATRIX

[75] Inventor: Melvin H. Keyes, Sylvania, Ohio

[73] Assignee: Owens-Illinois, Inc., Toledo, Ohio

[22] Filed: Sept. 10, 1973

[21] Appl. No.: 395,975

[44] Published under the second Trial Voluntary Protest Program on March 2, 1976 as document No. B 395,975.

[52] U.S. Cl. .................................. 195/68; 195/63; 195/DIG. 11

[51] Int. Cl.² .......................................... C07G 7/02

[58] Field of Search ................ 195/63, 68, DIG. 11

[56] References Cited

UNITED STATES PATENTS

| | | | |
|---|---|---|---|
| 2,717,852 | 9/1955 | Stone | 195/63 X |
| 3,666,627 | 5/1972 | Messing | 195/63 |
| 3,705,084 | 12/1972 | Reynolds | 195/63 |
| 3,850,751 | 11/1974 | Messing | 195/63 |

*Primary Examiner*—David M. Naff
*Attorney, Agent, or Firm*—Howard G. Bruss, Jr.; E. J. Holler

[57] ABSTRACT

Disclosed is a process for depositing and immobilizing an enzyme by causing an aqueous dispersion of said enzyme to flow through an inert, inorganic, porous, sorptive, dimensionally stable, fluid permeable supporting matrix to form a biologically active composite. The matrix is sufficiently porous to be enzyme and substrate permeable. Preferably, the supporting matrix is ceramic and is formed by compacting and sintering refractory oxide powders such as alumina.

8 Claims, 1 Drawing Figure

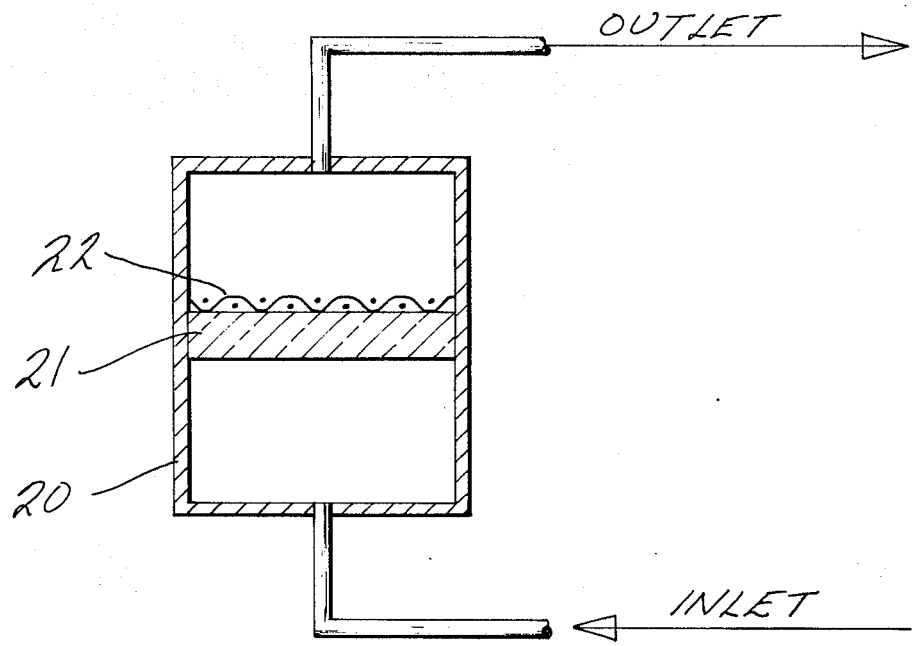

IMMOBILIZATION OF ENZYMES ON AN INORGANIC MATRIX

Enzymes are biologically active proteins which catalyze specific reactions. Enzymes have been used for a wide variety of industrial and research applications, particularly in fermentation, pharmaceuticals, medical research, and food processing. They are highly specific in their biological activity and generally do not generate significant quantities of undesirable by-products.

Recently attempts have been made to chemically or physically immobilize enzymes on various supports in the interest of efficient recovery and reuse. In the past, enzymes have been immobilized by attachment to inorganic supporting matrices by covalent coupling, adsorption, and ionic bonding. Covalent coupling of enzymes to water insoluble supports has been intensively investigated. Most of the supports have been organic polymers although recent reports have appeared where coupling agents have been used to attach enzymes to ceramic materials. For instance, U.S. Pat. No. 3,519,538 describes the use of silane coupling agents to attach enzymes to inorganic supports such as glass or alumina.

Adsorption of enzymes to water insoluble supports, whether organic or inorganic, has been the simplest insolubilization technique. It has been attractive because it requires merely exposing the enzyme in solution to the support material. The ease of adsorption, however, is offset by the corresponding ease of desorption. U.S. Pat. No. 3,556,945 discloses one technique for adsorption of enzymes to porous glass supports.

Another technique involves bonding the enzyme to the support in the presence of substrate and thus apparently blocking the active sites of the enzyme to avoid reaction of these sites with the support. Powdered glass and alumina are used for these applications in U.S. Pat. No. 3,666,627.

Further details on such prior art techniques can be found in the book entitled "*Biochemical Aspects of Reactions on Solid Supports,*" edited by George R. Stark, Academic Press, New York, N.Y. (1971): the article entitled "*Enzymes Immobilized on Inorganic Carriers*" by H. H. Weetall apperaing in *RESEARCH/DEVELOPMENT*, December (1971); the article entitled "*The Potential Applications of Molecular Inclusion to Beer Processing*" by R. A. Messing appearing in the December 1971 issue of the *BREWER'S DIGESTS*; U.S. Pat. Nos. 3,512,987 and 3,167,485.

More recently, processes have been proposed where ultrafiltration membranes serve to separate the reaction products from the enzyme and substrate in an enzyme reaction mixture. According to this technique, the enzyme and substrate are mixed and reacted in a reaction chamber and the reaction mixture is exposed to an ultrafiltration membrane, the porosity of which has been preselected to be permeable to the reaction product while retaining the substrate and enzyme. In this manner, the enzyme may be retained for reuse and need only be present in the catalytic amounts regardless of the amount of product produced.

Such ultrafiltration processes are disclosed in U.S. Pat. No. 3,720,583, the publication entitled "*Biotechnology and Bioengineering,*" Volume 12, page 615 (1970); and in the article by D. I. C. Wang, A. J. Sinskey, and T. A. Butterworth entitled, "*Enzyme Processing Using Ultrafiltration Membranes,*" Membrane Science Technology: Industrial Biological Waste Treatment Processes, Process Symposium 1969 (Pub. 1970), 98–119.

These ultrafiltration processes are specifically designed to prevent the permeation of substrate and enzyme from a reaction chamber and do not concern the formation of immobilized enzymes on supporting matrices.

While the discovery and the use of immobilized enzymes is superior to soluble enzyme reaction systems, such techniques have not been readily adopted to the formation of shaped integral rugged inorganic enzyme supports for pressurized flow-through reaction cells.

A need exists, therefore, for a process of preparing biologically active, fluid permeable composite, membranes in various geometrical configurations which are porous, strong and dimensionally stable so that they are capable of effecting enzyme reactions in a flow-through reaction chamber. The present invention provides such membranes.

Basically, the present invention involves flowing an aqueous dispersion of an active enzyme through an inert, inorganic, porous, sorptive, dimensionally stable, fluid permeable, supporting matrix to form a fluid permeable biologically active composite membrane. It is important for the matrix to be sufficiently porous to be permeable to enzyme as well as the substrate that will be subsequently processed therein.

The invention will be further explained in conjunction with the drawing which is a schematic pressure cell for carrying out enzymes deposition and reactions according to the present invention.

In carrying out the present invention, enzymes in aqueous dispersion are immobilized on an inert, porous, inorganic, fluid permeable, dimensionally stable, supporting matrix. The driving force for this deposition is provided by the application of pressure to a reservoir of the dispersion of enzyme in contact with the porous matrix. It is important for the matrix to be sufficiently porous to be fluid permeable and pass the enzyme so that substantial amounts of enzymes are present in the permeate passing through the matrix. In this regard, the enzyme is not deposited on the matrix by a filtration process (e.g. ultrafiltration) because the matrix itself is enzyme permeable.

The mechanism or theory for this invention is not presently understood, although the improved results have been clearly demonstrated. It is not known why the enzyme is immobilized more effective by flowing an aqueous dispersion thereof through the porous supporting matrix as compared with impregnating or soaking under static conditions.

Any enzyme which can be prepared in aqueous dispersion can be used, including a wide variety of enzymes which may be classified under three general headings; hydrolytic enzymes, redox enzymes, and transferase enzymes. The first group, hydrolytic enzymes, include proteolytic enzymes which hydrolyze proteins, e.g., papain, ficin, pepsin, trypsin, chymotrypsin, bromelin, keratinase, carbohydrases which hydrolyze carbohydrates, e.g., cellulase, amylase, maltase, pectinase, chitanase; esterases which hydrolyze esters, e.g., lipase, cholinesterase, lecithinase, alkaline and acid phosphatases; nucleases which hydrolyze nucleic acid, e.g., ribonuclease, desoxyribonuclease; and amidases which hydrolyze amines, e.g., arginase, asparaginase, glutaminase, histidase, and urease. The second group are redox enzymes that catalyze oxidation or reduction reactions. These include glucose oxidase, xanthine oxidase, catalase, peroxidase, lipoxidase, and cytochrome reductase. In the third group are transferase enzymes that transfer groups from one molecule to another. Examples of these are glutamicpyruvic transaminase, glutamic-oxalacetic transaminase, transmethylase, phosphopyruvic transphosphorylase. It should be noted that the enzyme can be used alone or in various combinations.

In that some enzymes may be rather impure, it is not known whether they all form true solutions in water. Accordingly, the term "dispersion" is used to include solutions, suspensions, and emulsions of enzymes.

The composition of the inorganic supporting matrix is not particularly critical as long as it is inert, dimensionally stable, and sufficiently porous to be fluid permeable and sorptive enough to retain enough enzyme to form a biologically active composite membrane.

In this regard, the matrix must be sufficiently porous to be enzyme permeable as well as permeable to the substrate which will eventually be converted thereby. This enzyme permeability is evidenced by the fact that substantial amounts of enzyme are present in the permeate passing through the matrix under deposition to form the biologically active composite membrane. Similarly, substantial amounts of substrate can be present in the permeate through the biologically active composite membrane if the flow rate of substrate is too high for complete conversion. This indicates that the substrate is not being physically "filtered out" by the membrane. In fact, it is important for the substrate to permeate and flow through the biologically composite membrane so that intimate contact with the enzyme immobilized in and on the membrane can be achieved.

In the commercially significant embodiments of the present invention, the biologically active composite membrane will exhibit at least about 0.001 International Units (I.U.) of activity per cubic centimeter of membrane.

An International Unit of biological activity has been defined as the amount of active enzyme which converts substrate to product at the rate of one micromole per minute.

It has been found that porous matrix having a volume porosity in the range of 10 percent to 80 percent and preferably in the range of 15–50 percent are quite suitable for the present purposes. The pore size of the support is critical in that it should not be so small as to prevent or inhibit fluid permeability in the resulting biologically active membrane. Average pore size diameters in the range of 0.01 micron to 10 microns are suitable for most applications with 0.01 to 2 being preferred for efficiency and economy.

The porous support can be formed by compacting and sintering refractory ceramic oxide powders such as alumina powder, zirconia powder, magnesia powder, silica powder, thoria powder, glass powder, powdered clay, powdered talc and the like.

Porous, inert, rigid, dimensionally stable refractory supports can be prepared by compacting such refractory oxide powders to form a "green compact" of the desired configuration. The green compacts are then fired for a time and at a temperature sufficient for sintering to yield porous, inert, rigid, dimensionally stable, fluid permeable refractory support. The sintering should not be at a temperature or for a time which would cause collapsing or coalescence of the particles to form a non-porous body. A convenient indication of the degree of sintering is a comparison of the actual density of the fired compact as compared to the the theoretical density of the oxide being fired. Of the many oxides which can be used for the present purposes, alumina is preferred for its chemical durability and ease of fabrication.

In forming the support from the powdered refractory oxide, the powdered particle size is selected to yield a sintered compact having a porosity and pore size in the range set forth above. The techniques for compaction and sintering of the porous supports are well-known in the art and form no part of the present invention. Suffice it to say that compacting pressures in the range of 1,000 p.s.i. to 10,000 p.s.i. and sintering temperatures in the range of 1300° to 1700°C. are commercially expedient. Additional details on compacting and sintering of refractory oxides can be obtained from the book "*Oxide Ceramics*" by E. Ryshkewitch, published in 1960 by Academic Press, New York, New York.

The porous supporting matrix can also be in the form of porous 96 percent silica glass such as is disclosed in the article entitled "*Properties of Some VYCOR-Brand Glasses*" by M. E. Nordberg appearing at page 299 in Volume 27, No. 10 of the Journal of the American Ceramic Society (1944). Other such porous glasses are disclosed in U.S. Pat. Nos. 2,215,039 and 3,556,945, the disclosure of which are incorporated by reference.

The porous matrix can also be made of porous carbon, a porous metal such as porous silver or porous stainless steel.

The porous matrix can be in any geometric shape such as rods, cylinders, discs, plates, tubes, bars, and blocks so long as it can be positioned in a flow through pressure cell in a deposition process as will be described below.

In the deposition of enzyme, a dilute aqueous dispersion of enzyme is employed. The amount of enzyme to be added to the aqueous dispersion will depend upon the area of the matrix support to be deposited, the degree of activity desired in the final membrane, the activity of the enzyme preparation being used, and the particular enzyme material being used. Usually, enzyme concentrations in the range of $1 \times 10^{-5}$ percent to 10 percent by weight of the aqueous dispersion are suitable. The optimal amount for a given system can be readily determined, because the use of too little enzyme will result in a membrane of low activity, while the use of an excessive amount of enzyme is economically wasteful.

In depositing an immobilizing the enzyme on the supporting matrix and aqueous dispersion of the enzyme is placed in a chamber equipped with the supporting matrix. The matrix is positioned in the chamber such that the aqueous dispersion of enzyme must pass therethrough when pressure is applied to the chamber. This type of device is called a "flow-through" deposition chamber.

The pressure required to deposit the enzyme on the matrix will depend on the porosity and thickness of the matrix employed. The pressure should be sufficient to cause the enzyme to permeate and flow through the membrane. In a commercially significant embodiment of the present invention, the pressure will be in the range of about 10 p.s.i. to about 1000 p.s.i.

The enzyme deposition to form the biologically active composite membrane can be carried out in a conventional pressure reaction cell 20 as shown in the drawing.

The particular cell employed in the examples that follow is an Amicon Model 420 high-pressure ultra-filtration cell in which the ultrafiltration membrane has been replaced with the supporting matrix 21. Matrix 21 is sealed into cell 20 to prevent leakage at the interface therebetween. Matrix 21 is supported by inert grid 22 in the form of a stainless steel screen so that the matrix will not be dislodged by the pressure in the cell.

A pressure cell like the one shown in the drawing can also be used to carry out the enzyme reaction merely by leaving the biologically active membrane in place after immobilizing the enzyme thereon, charging the pressure cell with substrate and pressuring the cell to cause the substrate to permeate and flow through the membrane to affect the reaction.

Temperatures are not critical as long as the temperature is kept above the freezing point of the enzyme dispersion, and below a temperature at which the enzyme will become thermally denatured. Although some enzymes can tolerate temperatures in the neighborhood of 110°C, temperatures between 0° and 50°C are usually satisfactory with room temperature a convenient working temperature.

The time required for immobilizing enzyme on the matrix will vary according to the concentration of enzyme, the surface area of the matrix being deposited, the temperature, and the flow rate through the matrix. Usually, time periods ranging from 5 minutes to an hour are satisfactory.

In the Examples that follow, all parts are parts by weight, all percentages are weight percentage, and all temperatures are in °C. unless stated otherwise.

EXAMPLE 1

Part A

Preparation of the Support Matrix

Porous supporting matrices in the form of discs are prepared from a fine alumina powder having an average particle diameter of about 1 micron. (Such alumina powder is available from Alcoa under the designation of "A-16".) A compaction mixture is formed by ball-milling 3 percent polyvinyl alcohol, ½ percent stearic acid, 25 percent $H_2O$, with the balance being alumina powder. The polyvinyl alcohol and the stearic acid serve as compaction aids. The milled powder is dried at 150°C. under vacuum.

The dried alumina powder is then compacted in a ram press into discs of ¾ inch in diameter and 55 mils thickness under 6,000 p.s.i. The discs weigh about 1 to 1.5 grams each.

If desired at this point, the alumina powders can alternatively be extruded in the form of a porous alumina tube or other shape using a conventional extrusion or other processing equipment. The further processing is described in terms of the discs although tubes or other geometric shapes can be processed in the same fashion.

The discs are sintered by heating gradually to 1,500°C. and then maintaining this temperature for 2 hours. The discs are then allowed to cool to room temperature over several hours.

The resulting discs are porous, fluid permeable, rigid, dimensionally stable, and sorptive. Supporting matrices can also be formed in this manner from refractory materials, powdered titania, powdered zirconia, powdered thoria, powdered glass, and fine clay.

The faces of the resulting sintered discs are then ground so that they are substantially flat and parallel.

The resulting discs have a porosity of about 20 to 40 percent with an average pore diameter of about 0.1 micron.

Because of the chemical and thermal stability of the alumina support matrix, it can be reconditioned for reuse, if desired, after the immobilized enzyme has finally lost most of its activity. It is necessary only to place the disc in a furnace and heat at 800°C. for 2 hours. This serves to remove enzyme and other entrapped residual organic materials as well as to dehydrate and reactivate the surface of the alumina. Thus, a single alumina support can be used repeatedly.

Part B

Pressure Deposition of Enzyme

A 0.01 percent by weight dispersion of chymotrypsin is prepared from enzyme material having an activity of 45 I.U./mg, based on benzoyltyrosine ethyl ester (BTEE) conversion. The pH of the aqueous dispersion is adjusted to 6.5 with a 0.08M tris (hydroxymethyl) aminomethane (TRIS) solution containing calcium chloride (0.1M) as a stabilizer for the enzyme.

A porous disc shaped alumina matrix prepared in Part A having an average pore size of about 0.04 microns and a porosity of 35 percent is placed in the pressure deposition cell as described in conjunction with the drawing.

Nitrogen pressure varying from about 10 p.s.i. to about 1,000 p.s.i. is applied to the cell while its contents are at room temperature and the enzyme dispersion permeates and flows through the matrix for several minutes. Enzymes are present in the permeate. After about 150 ml of permeate have been collected, the pressure is released and the enzyme has been immobilized in an active form on the porous, alumina matrix to form a fluid permeable, rigid, dimensionally stable biologically active composite membrane.

Part C

Procedure for Determining Enzyme Activity

It is known that the flow rate of substrate solution passing through a membrane containing immobilized enzyme has a definite effect on the percent conversion that is obtained. Therefore, to reduce the complexity of the system and calculate a flow rate-independent initial velocity, the procedure now to be described is employed in the Examples.

The activity in International Units of the enzyme immobilized on the biologically active composite membrane is determined from the equation $$I.U. = \frac{\Delta C}{\frac{1}{Q}}$$

where I.U. is activity in micromoles of substrate converted per minute in the flow through reactor illustrated in the drawing at steady state conditions. C is concentration of substrate in micromoles per liter. $\Delta C$ is the change in concentration of substrate upon flowing through the membrane. Q is flow rate through the membrane in liter per minute. In the Examples, the I.U. are determined as the slope of a line passing through the origin and coincident with the straight line portion of the plot obtained by plotting $\Delta C$ versus $1/Q$.

The substrate concentration changes are determined spectrophotometrically from UV absorption measurements in the usual manner at the appropriate wave length for the specific enzyme under consideration except for examples involving urease where the formation of ammonium ions is measured by a cation electrode.

The activity of the membrane prepared in Part B is determined in the pressure cell by the procedure described above using a BTEE solution at pH 5 as described by B. C. Hummel in Volume 37 of the Canadian Journal of Biochem. Physiol. at page 1393 (1959).

The pressure applied to the reaction cell is varied from 200 up to 1000 p.s.i. to provide several different flow rates to use in the calculation of enzyme activity. The increase in optical density at 256 nm is used to monitor the formation of reaction product.

This analysis gives an activity of 0.622 I.U. of chymotrypsin for the biologically active composite membrane. The membrane is stored for 93 days in the same buffer solution as used in the assay. The activity is then measured again and found to be 0.023 I.U.

As a control, an alumina disc with average pore size of 0.15 micron is placed in the above 0.01 percent chymotrypsin dispersion for ½ hour. After adsorption for ½ hour the disc is washed thoroughly with the TRIS buffer mentioned above and stored at 2°–5°C. The activity, as measured in the same way as described above, is the equivalent of 0.01 I.U. of soluble chymotrypsin with respect to BTEE. 9 days after preparation, no activity could be detected on the disc.

The enhanced activity of the membrane toward BTEE in this example may in part be attributable to the presence of calcium ion in the enzyme (chymotrypsin) solution. In that the calcium chloride is present in both the control and the example, its effect is "blanked out" with respect to the present invention. Similar beneficial effects of calcium ion have been noted for conversion of BTEE in solution phase with the enzyme chymotrypsin by S. P. Colowich and N. O. Caplan as reported in Methods in Enzymology Volume II, pages 8–26, Academic Press, Inc., New York, N.Y. (1955).

Part D

The procedure of Part B and C are repeated except that the alumina matrix has an average pore size of about 0.23 microns and a free volume of 34 percent.

When assayed after three days, as in Part C, the activity of the biologically active composite membrane is found to be 0.578 I.U. After 33 days, the activity has dropped to 0.259 I.U. and after 60 days, to 0.052 I.U.

Part E

The procedure of Part B and C are repeated except that a sintered porous alumina tube is used as the support matrix. The tube is 6.85cm long with an outer diameter of 0.56cm and an inner diameter of 0.297cm and has an average pore size of 0.21 microns and a free volume of 36 percent.

The enzyme-alumina composite matrix is assayed with BTEE substrate as in Part C and the activity is determined to be 0.268 I.U.

EXAMPLE 2

A 0.071 percent by weight xanthine oxidase solution is prepared by dissolving the enzyme (activity 0.5 I.U./mg) in distilled water containing sodium salicylate ($9 \times 10^{-4}$M) and ethylene-diaminetetraacetic acid ($4 \times 10^{-4}$M). The pH of the resulting solution is 8.1.

The procedures of Part B of Example 1 are employed except that the porous alumina disc used as the matrix has an average pore diameter of 0.15 microns and a porosity of 35 percent.

A total of 500 ml of the xanthine oxidase solution is permeated through the disc during deposition at a pressure of 1000 p.s.i.

The activity of the membrane is determined as in Example 1 using a buffered $1.0 \times 10^{-4}$M xanthine solution of pH 8.3, containing pyrophosphate (0.1M) and ethylenediaminetetraacetic acid ($3 \times 10^{-4}$M). Optical density changes at 295 nm are used to measure the change in concentration of xanthine. One day after preparation, the activity of the membrane is $3.33 \times 10^{-2}$ I.U. After six weeks storage in the buffer solution, in the absence of substrate, the membrane activity is $5.2 \times 10^{-2}$ I.U.

EXAMPLE 3

A 1.0 percent by weight histidase solution is prepared by dissolving histidase (4.8 I.U./mg) in distilled water. This solution is centrifuged at 1000g for five minutes to remove insoluble impurities. The supernatant is then diluted with 7.5 parts of a 0.1M buffer solution of 2-amino-2-methyl-1, 3-propanediol (AMPD). Reduced glutathione is added in an amount equal to 76 times the weight of histidase present. This serves to inhibit oxidation of the histidase. The resulting solution is then diluted with distilled water to give a 0.0019 percent by weight solution of histidase.

The procedures of Example 1 are employed except that the porous alumina disc used as the matrix has an average pore diameter of 0.08 microns and a porosity of 35 to 40 percent. Five hundred ml of the histidase solution is permeated through the disc at a pressure of up to 1000 p.s.i. to form the biologically active composite membrane.

The activity of the membrane is determined as in Example 1 using a substrate solution of histidine ($4 \times 10^{-3}$M) containing 2-amino-2-methyl-1, 3-propanediol (0.01M) and dithiothreitol ($1 \times 10^{-4}$M) having a pH of 9.2. The change in concentration of histidine is followed by optical density changes at 277nm.

The day after preparation of the membrane, the activity is found to be 1.1 I.U. This value drops to $8.0 \times 10^{-4}$ I.U. after two weeks and $4.0 \times 10^{-4}$ I.U. after 5 weeks. The membrane is stored in a histidine-free buffer solution between measurements.

EXAMPLE 4

A urease solution is prepared by dissolving 4 parts of urease (25 I.U./mg) in 300 parts of distilled water which had been adjusted to a pH of 8.5 with 0.01M triethanolamine.

The procedures of Example 1 are employed except that the porous alumina disc used as the support matrix has an average pore diameter of 0.4 microns and a porosity of 35 percent. A pressure up to 1000 p.s.i. is used to permeate 150 ml of the urease solution through the alumina support.

The resulting composite membrane is assayed with a 0.05M urea solution which is 0.01 molar in triethanolamine and has a pH of 6.7. A cation specific electrode is used to monitor the production of ammonium ions generated from the hydrolysis of urea as it passes through the ureasealumina composite membrane.

The activity of the membrane is determined as in Example 1. One day after preparation, the membrane is found to have an activity of 2.6 I.U. which decreases to $1.7 \times 10^{-2}$ I.U. after 1 month. When stored for one week in $1.0 \times 10^{-3}$M mercaptoethanol, the activity of the urease is partially regenerated and a value of $5.5 \times 10^{-2}$ I.U. can be obtained.

Having thus described the invention, what is claimed is:

1. A process for depositing and immobilizing an enzyme on an inert, inorganic, porous, sorptive, dimensionally stable, liquid permeable metal oxide supporting matrix having been formed by compacting and sintering a refractory metal oxide powder, said matrix being sufficiently porous to be enzyme and substrate permeable, and having a porosity in the range of about 10 percent to about 80 percent and an average pore diameter in the range of about 0.01 to 10 microns, said process comprising contacting an aqueous dispersion of said enzyme with said matrix, applying at least about 10 psig pressure to said dispersion to cause substantial amounts of said dispersion to flow through said matrix, maintaining the flow of said dispersion through said matrix for a sufficient time period of at least about 5 minutes to immobilize said enzyme directly on said matrix to form an enzymatically active composite.

2. The process of claim 1 wherein said pressure is in the range of about 10 psig to about 1000 psig.

3. The process of claim 1 wherein said enzymatically active composite has a biological activity of at least about 0.001 International Units per cubic centimeter.

4. The process of claim 1 wherein said matrix has a porosity in the range of about 15 percent to 50 percent.

5. The process of claim 1 wherein said matrix has an average pore diameter in the range of about 0.01 to about 2 microns.

6. The process of claim 1 wherein said aqueous dispersion of enzyme contains said enzyme in the proportion of $1 \times 10^{-5}$ percent to about 10 percent by weight of said dispersion.

7. The process of claim 3 wherein said refractory oxide powder is alumina.

8. The process of claim 1 wherein said time period is in the range of about 5 minutes to about 1 hour.

* * * * *